(12) United States Patent
Rimlinger et al.

(10) Patent No.: US 7,662,131 B2
(45) Date of Patent: Feb. 16, 2010

(54) LIQUID-INJECTION SYRINGE ASSEMBLY, AND A SHEATH FOR THE ASSEMBLY

(75) Inventors: Thierry Rimlinger, L'Isle d'Abeau (FR); Michel Pouget, Domarin (FR); Thierry Peysson, Pusignan (FR); Philippe Dodier, St Foy les Lyon (FR)

(73) Assignee: Compagnie Plastic Omnium, Lyons (FR)

( * ) Notice: Subject to any disclaimer, the term of this patent is extended or adjusted under 35 U.S.C. 154(b) by 0 days.

(21) Appl. No.: 10/421,736

(22) Filed: Apr. 24, 2003

(65) Prior Publication Data

US 2004/0092884 A1 May 13, 2004

(30) Foreign Application Priority Data

Apr. 25, 2002 (FR) .................................. 02 05235

(51) Int. Cl.
*A61M 5/00* (2006.01)
(52) U.S. Cl. ........................................ 604/110; 604/187
(58) Field of Classification Search .................. 604/110, 604/181, 187, 192, 197, 198, 221, 222
See application file for complete search history.

(56) References Cited

U.S. PATENT DOCUMENTS 4,932,940 A * 6/1990 Walker et al. ............... 604/110
5,163,918 A * 11/1992 Righi et al. ................. 604/198
5,342,320 A 8/1994 Cameron
6,638,255 B1 * 10/2003 Weber ........................ 604/181
2004/0147875 A1 * 7/2004 Wallace et al. .............. 604/110

FOREIGN PATENT DOCUMENTS

EP      0 467 173 A1    1/1992

* cited by examiner

*Primary Examiner*—Kevin C Sirmons
*Assistant Examiner*—Phillip Gray
(74) *Attorney, Agent, or Firm*—Oliff & Berridge, PLC

(57) ABSTRACT

The assembly comprises a body forming a reservoir for the liquid, the body being provided with a liquid-injection needle, a plunger mounted to be axially movable in the body between a ready position and an end-of-injection position, and a sheath in which the body is mounted to be axially movable between an active position in which the needle projects from a distal end of the sheath, and a protecting position in which the needle is retracted inside the sheath. The assembly also comprises means for axially securing the plunger and the sheath in a relative position of said plunger and said sheath serving firstly to position the body in its protecting position relative to the sheath and secondly to position the plunger in its end-of-injection position relative to the body.

10 Claims, 2 Drawing Sheets

LIQUID-INJECTION SYRINGE ASSEMBLY, AND A SHEATH FOR THE ASSEMBLY

The present invention relates to a liquid-injection syringe assembly and to a sheath for the assembly.

BACKGROUND OF THE INVENTION

In the prior art, and in particular in U.S. Pat. No. 5,562,626, a liquid-injection syringe assembly of the following type is disclosed:
- a tubular syringe body forming a reservoir for the liquid, the body being provided with a distal end carrying a liquid-injection needle;
- a syringe plunger mounted to be axially movable in the body between a ready position and an end-of-injection position; and
- a tubular sheath in which the syringe body is mounted to be axially movable between an active position in which the needle projects from the distal end of the sheath, and a protecting position in which the needle is retracted inside the sheath.

A syringe assembly of the above type is generally provided with means enabling the needle to be retracted automatically into the sheath so as to ensure that a person handling the syringe assembly after it has been used normally, i.e. after liquid has been injected into the body of a patient, cannot be accidentally pricked by the needle.

When the syringe body is in its protecting position relative to the sheath, it is appropriate to prevent any accidental return of the injection needle towards its position in which it projects from the sheath.

For this purpose, U.S. Pat. No. 5,562,626 purposes axial securing means for securing the syringe body and the sheath axially, said means being activated while the syringe body is in its protecting position, in which the needle is retracted into the sheath. The axial securing means comprise a expansion collar integrally molded with the body of the syringe, which means that said body is specific to the syringe assembly described in U.S. Pat. No. 5,562,626.

Unfortunately, certain medical substances are packaged directly in standard syringe bodies (prefilled syringes), generally made of glass, and closed by pistons which are subsequently connected to plungers for actuating the pistons.

OBJECTS AND SUMMARY OF THE INVENTION

An object of the invention is to provide a syringe assembly of the above-specified type suitable for being fitted with a relatively standard syringe body, e.g. made of glass, said assembly being fitted with means that are effective, after the syringe has been used, in preventing any accidental return of the injection needle towards its position projecting from the sheath.

To this end, the invention provides a liquid-injection syringe assembly of the above-specified type comprising axial securing means for securing the plunger and the sheath axially in a relative position of said plunger and said sheath serving both to position the body in its protecting position relative to the sheath, and to position the plunger in its end-of-injection position relative to the body.

According to other characteristics of various embodiments of the syringe assembly:
- the assembly comprises:
  - return means for resiliently returning the body towards its protecting position;
  - retaining means for retaining the body in its active position relative to the sheath, opposing the resilient force of the return means; and
  - a member carried by the plunger for co-operating with the retaining means to deactivate them when the assembly is in an end-of-injection configuration;
- the axial securing means for securing the plunger and the sheath comprising axially opposing distal and proximal securing abutments between which the member for deactivating the retaining means is designed to snap-fasten;
- in its position snap-fastened between the securing abutments, the member for deactivating the retaining means can co-operate with each of said securing abutments;
- the securing abutments are defined by axial tabs formed in the sheath and retractable by radial elastic deformation;
- the member for releasing the retaining means is formed by a flange integrally molded with the plunger and referred to as the plunger flange;
- the syringe body is provided with a proximal end having a flange referred to as the body flange, the retaining means comprising axially opposing retaining abutments between which the body flange is retained, said retaining abutments being defined by an internal retaining shoulder of the sheath and by at least one axial tab formed inside said sheath and retractable by radial deformation;
- when the plunger is in its end-of-injection position relative to the body, the body flange is designed to become snap-fastened between the securing abutments in such a manner that the body flange can co-operate with the distal securing abutment and the member for deactivating the retaining means can co-operate with the proximal securing abutment;
- the return means for returning the syringe body towards its protecting position comprise a thrust spring bearing firstly against an internal "return" shoulder of the sheath interposed between the distal end of the sheath and the retaining shoulder, and also against the flange of the syringe body;
- the sheath carries external grip means for being held by the fingers of a user to inject the liquid by moving the proximal end of the plunger axially towards the grip means; and
- the grip means comprise an external shoulder on the sheath.

The invention also provides a sheath for a liquid-injection syringe assembly, the sheath being for an assembly as defined above.

BRIEF DESCRIPTION OF THE DRAWINGS

The invention will be better understood on reading the following description given purely by way of example and made with reference to the accompanying drawings, in which.

MORE DETAILED DESCRIPTION

Figure 1:
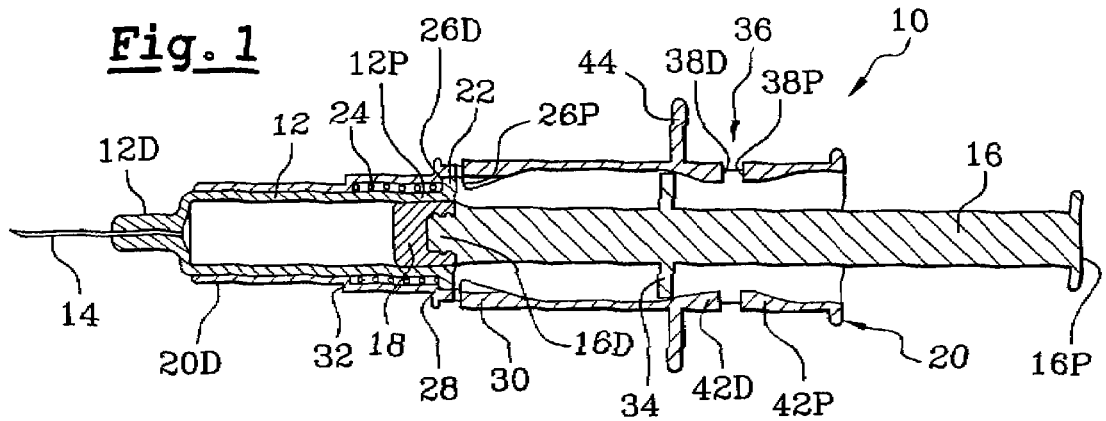
FIGS. 1 to 3 are axial section views of a syringe assembly constituting a first embodiment of the invention shown in three configurations of use of said assembly.
Figure 2:
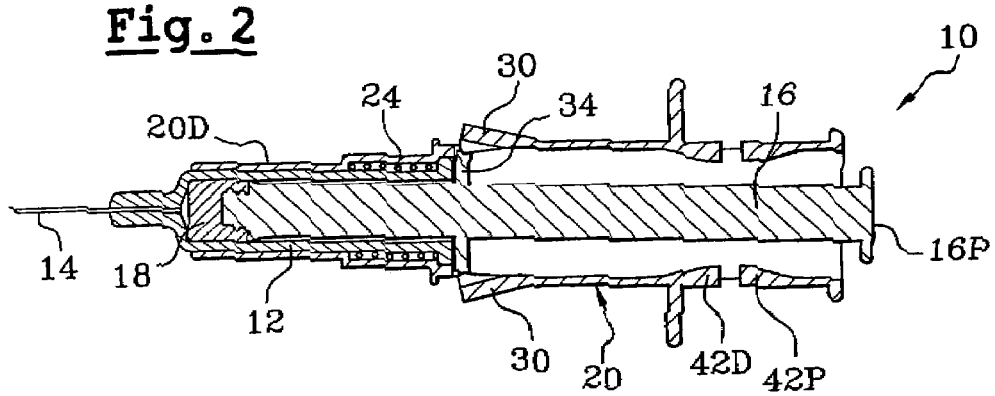
Figure 3:
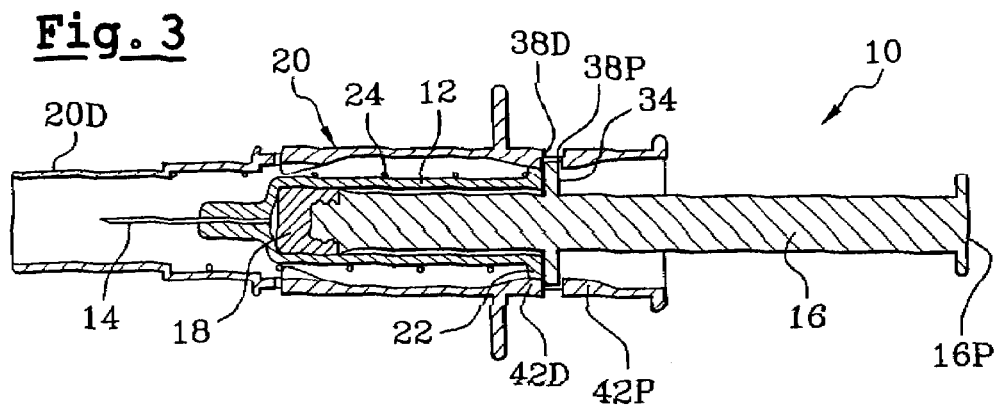

FIGS. 1 to 3 show a liquid-injection syringe assembly, in particular an assembly for injecting a medicinal liquid, constituting a first embodiment of the invention. This syringe assembly is given overall reference 10.

The syringe assembly 10 comprises a tubular syringe body 12 of conventional type, forming a reservoir for the liquid. The body 12 carries a needle 14 for injecting the liquid.

The syringe assembly 10 also comprises a plunger 16 that is axially displaceable in the body 12 between a ready position as shown in FIG. 1, and an end-of-injection position corresponding to the end of injecting liquid, as shown in FIG. 2.

In the description below, the terms "proximal" and "distal" are used to designate being axially close or far from the end of the plunger 16 that is to be actuated by a user.

The plunger 16, e.g. made of plastics material, comprises a proximal end 16P outside the body 12, and a distal end 16D inside the body 12 and carrying a conventional piston 18. The proximal end 16P forms a drive end of the plunger 16.

The syringe assembly 10 comprises a tubular safety sheath 20 in which the body 12 of the syringe is received. The sheath 20 is circularly cylindrical and is made out of plastics material, for example, and where appropriate of sufficient transparency for it to be possible to view the liquid contained in the body 12 of the syringe or markings carried on said body 12.

The syringe body 12 is mounted to be axially displaceable in the sheath 20 between an active position in which the needle 14 projects from a distal end 20D of the sheath, and a protecting position in which the needle 14 is retracted inside the sheath 20. The active position is shown in FIGS. 1 and 2. The protecting position is shown in FIG. 3.

It should be observed that the syringe body 12 has a distal end 12D carrying the needle 14 and a proximal end 12P provided with a flange, referred to as the body flange 22.

The syringe assembly 10 includes retaining means for retaining the body 12 in its active position relative to the sheath 20. These retaining means oppose the resilient force of return means comprising a thrust spring 24.

In the example shown, the retaining means comprise axially opposed abutments referred to as the distal retaining abutments 26D and the proximal retaining abutments 26P. The distal retaining abutment 26D is defined by an internal shoulder of the sheath 20 referred to as a retaining shoulder 28. The proximal retaining abutment 26P is defined by at least one axial tab 30 formed inside the sheath 20 and retractable by radial deformation, e.g. by elastic radial deformation.

The sheath 20 preferably has two diametrically-opposite axial retaining tabs 30.

When the syringe assembly 10 is in a ready configuration, the body flange 22 is retained axially between the retaining abutments 26D and 26P as is shown in FIG. 1.

The spring 24 bears firstly against an internal shoulder of the sheath 20 referred to as the return shoulder 32, and secondly against the body flange 22. It should be observed that the return shoulder 32 is interposed between the distal end 20D of the sheath and the retaining shoulder 28.

The means for retaining the body 12 in its active position are designed to be deactivated by means of a member carried by the plunger, e.g. a flange integrally molded with the plunger 16, referred to as plunger flange 34.

When the syringe assembly 10 is in its configuration at the end of injecting liquid, as shown in FIG. 2, the plunger flange 34 co-operates with ramps formed on the axial tabs 30 so as to deform said tabs. This has the effect of moving the tabs 30 radially away from the body flange 22, thereby releasing the means for retaining the body 12 in its active position.

Once the retaining means have been released, the spring 24 resiliently urges the syringe body 12 towards its protecting position as shown in FIG. 3.

The syringe assembly 10 has axial securing means 36 for securing the plunger 16 and the sheath 20 axially in a relative position as shown in FIG. 3. This relative position of the plunger 16 and of the sheath 20 serves firstly to position the body 12 in its protecting position relative to the sheath 20, and secondly to position the plunger 16 in the position it occupies relative to the body 12 at the end of injection.

In the example shown, the axial securing means 36 comprise axially opposite abutments referred to as distal securing abutments 38D and proximal abutments 38P, and the plunger flange 34 is designed to become snap-fastened between them.

The securing abutments 38D and 38P are defined by distal and proximal axial tabs 42D and 42P formed in the sheath 20, and retractable by radial elastic deformation.

The sheath 20 preferably has two diametrically-opposite pairs of axial tabs 42D and 42P, each pair comprising a distal tab 42D and a proximal tab 42P.

The sheath 20 carries external grip means for being held by the fingers of a user in order to inject liquid by moving the drive end 16P of the plunger axially towards the grip means.

In the example described, the grip means comprise two external radial tabs 44 secured to the sheath 20.

Prior to use, the syringe assembly 10 is in the ready configuration as shown in FIG. 1. Where appropriate, a removable needle-protecting cap (not shown in the figure) is engaged on the distal end 12D of the syringe body.

In this configuration, the plunger flange 34 is interposed axially between the retaining tabs 30 and the distal securing tabs 42D.

In order to inject the liquid, the user takes hold of the syringe assembly 10 in such a manner as to push the plunger 16 into the syringe body 12 by moving the end 16P of the plunger axially towards the grip tabs 44.

The user pushes in the plunger 16 until reaching the end-of-injection position shown in FIG. 2.

In the configuration of the syringe assembly 10 shown in FIG. 2, the axial tabs 30 for retaining the body 12 are moved radially away from the body flange 22 by the plunger flange 34.

Because the retaining abutments 26P carried by the tabs 30 have been retracted, when the user ceases to exert pressure on the drive end 16P of the plunger, the spring 24 relaxes, pushing the empty syringe body 12 towards its protecting position as shown in FIG. 3.

During the displacement of the syringe body 12 towards its protecting position relative to the sheath 20, the plunger flange 34 begins by co-operating with the distal securing tabs 42D in order to retract them radially, and then it snap-fastens between the securing abutments 38D and 38P, as shown in FIG. 3.

When the plunger flange 34 is in its position snap-fastened between the securing abutments 38D and 38P, it can co-operate with each of these securing abutments 38D, 38P.

Thus, when the syringe assembly 10 is in the configuration shown in FIG. 3, the needle 14 is retracted into the sheath 20. In addition, the plunger 16 is prevented from moving axially relative to the sheath 20 such that the body 12 can no longer be moved towards its active position by involuntary action on the plunger 16.

Any untimely separation of the flange 34 from the tabs 42D and 42P can be prevented by appropriately dimensioning the tabs 42D and 42P, in particular by restricting the clearance between the flange 34 and the abutments 38D and 38P.

It should be observed that the proximal tabs 42P have ramps that make it easier during initial assembly of the syringe assembly 10 to insert the plunger 16 into the sheath 20 in order to be connected to the piston 18 closing the syringe body 12 already received in the sheath 20.

Amongst the advantages of the invention, it should be observed that the body of the syringe assembly of the invention is of a simple shape that is well suited in particular for standardized glass or plastics manufacture and for use in a prefilled syringe.

The structure of the syringe assembly of the invention is very simple. It suffices to fit the syringe with the plunger 16, the one-piece sheath 20, and the spring 24 in order to obtain the assembly of the invention.

The syringe assembly of the invention requires the user to perform the same actions when operating it as are performed to operate a conventional syringe that does not include needle-retraction means.

The means for retaining the syringe body in its active position are automatically deactivated at the end of injection. The means for axially securing the plunger with the sheath are activated automatically when the user releases the pressure exerted on the plunger.

The above-described deactivation of the retaining means and activation of the axial securing means thus take place automatically while the user is handling the syringe assembly in one hand, performing actions that are entirely conventional.

Furthermore, the means for axially securing the plunger 16 to the sheath 20 are effective after the syringe has been used for preventing any accidental return of the injection needle towards its position projecting from the sheath.

Figure 4:
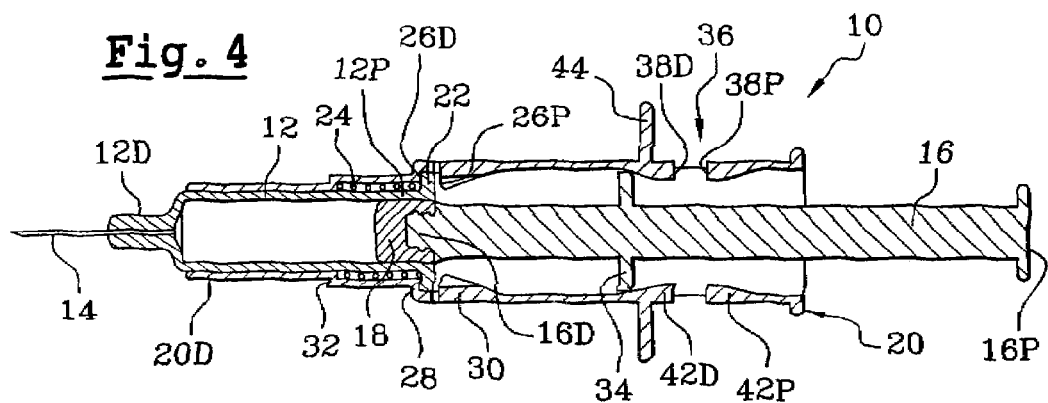
FIGS. 4 to 6 are views similar to the preceding figures of a syringe assembly constituting a second embodiment of the invention.
Figure 5:
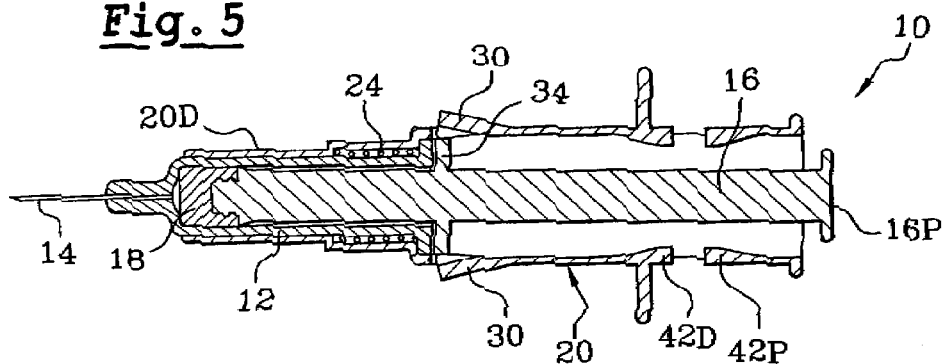
Figure 6:
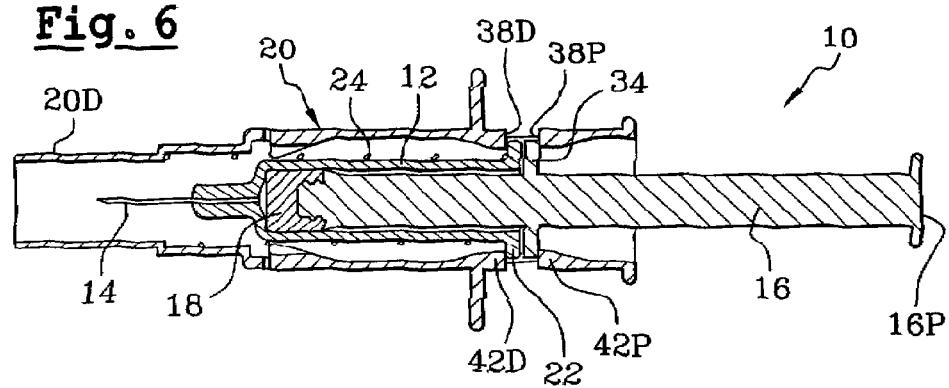

FIGS. 4 to 6 show a liquid-injection syringe assembly constituting a second embodiment of the invention. In these figures, elements analogous to those of FIGS. 1 to 3 are designated by references that are identical.

Prior to use, the syringe assembly 10 is in its ready configuration as shown in FIG. 4.

As in the first embodiment of the invention, in order to inject the liquid, the user takes hold of the syringe assembly 10 so as to push the plunger 16 into the syringe body 12 by moving the end 16P of the plunger axially towards the grip tabs 44.

The user pushes in the plunger 16 until it reaches the end-of-injection position shown in FIG. 5. In this configuration, the axial tabs 30 for retaining the body 12 are moved radially away from the body flange 22 by the plunger flange 34.

Under thrust from the spring 24, the body flange 22 is driven to snap-fasten between the securing abutments 38D and 38P as shown in FIG. 6. In this configuration, the body flange 22 can co-operate with the distal securing abutment 38D while the plunger flange 34 can co-operate with the proximal securing abutment 38P.

Thus, when the syringe assembly 10 in the configuration shown in FIG. 6 (needle 14 retracted inside the sheath 10), the plunger 16 and the body 12 are prevented from moving axially relative to the sheath 20, such that the body 12 can no longer be moved towards its active position.

The invention is not limited to the embodiments described above.

In particular, the needle 14 can be fitted to the body 12 using manual assembly means such as screw fastening means or snap-fastening means.

The means 26D and 26P for retaining the body 12 in its active position relative to the sheath 20 may also be deactivated even before the plunger 16 reaches the end-of-injection position. This can be achieved by appropriately adapting the shapes or the positions of the retaining abutments 26P carried by the tabs 30 and of the plunger flange 34.

Such an arrangement makes it possible to cause the needle 14 to be retracted, and thus the user to be protected, even if the user has not injected all of the liquid that is contained in the body of the syringe.

What is claimed is:

1. A liquid-injection syringe assembly of the type comprising:
    a tubular syringe body forming a reservoir for the liquid, the body being provided with a distal end carrying a liquid-injection needle;
    a syringe plunger mounted to be axially movable in the body between a ready position and an end-of-injection position; and
    a tubular sheath in which the syringe body is mounted to be axially movable between an active position in which the needle projects from the distal end of the sheath, and a protecting position in which the needle is retracted inside the sheath;
    the assembly including:
        return means for resiliently returning the body towards its protecting position;
        retaining means for retaining the body in its active position relative to the sheath, opposing the resilient force of the return means;
        a member carried by the plunger for co-operating with the retaining means to deactivate them when the assembly is in an end-of-injection configuration; and
        axial securing means for securing the plunger and the sheath axially in a relative position of said plunger and said sheath serving both to position the body in its protecting position relative to the sheath, and to position the plunger in its end-of-injection position relative to the body, comprising distal securing abutment and a proximal securing abutment, carried by the sheath, between which the member is designed to be snap-fastened, so that the member is in between the distal securing abutment and the proximal securing abutment.

2. A syringe assembly according to claim 1, wherein, in its position snap-fastened between the securing abutments, the member for deactivating the retaining means can co-operate with each of said securing abutments.

3. A syringe assembly according to claim 1, wherein the securing abutments are defined by axial tabs formed in the sheath and retractable by radial elastic deformation.

4. A syringe assembly according to claim 1, wherein the member for releasing the retaining means is formed by a flange integrally molded with the plunger and referred to as the plunger flange.

5. A syringe assembly according to claim 1, wherein the syringe body is provided with a proximal end having a flange referred to as the body flange, the retaining means comprising axially opposing retaining abutments between which the body flange is retained, said retaining abutments being defined by an internal retaining shoulder of the sheath and by at least one axial tab formed inside said sheath and retractable by radial deformation.

6. A syringe assembly according to claim 5, wherein, when the plunger is in its end-of-injection position relative to the body, the body flange is designed to become snap-fastened between the securing abutments in such a manner that the body flange can co-operate with the distal securing abutment and the member for deactivating the retaining means can co-operate with the proximal securing abutment.

7. A syringe assembly according to claim 5, wherein the return means for returning the syringe body towards its protecting position comprise a thrust spring bearing firstly against an internal "return" shoulder of the sheath interposed between the distal end of the sheath and the retaining shoulder, and also against the flange of the syringe body.

8. A syringe assembly according to claim 1, wherein the sheath carries external grip means for being held by the fingers of a user to inject the liquid by moving the proximal end of the plunger axially towards the grip means.

9. A syringe assembly according to claim 8, wherein the grip means comprise an external shoulder on the sheath.

10. A sheath for a liquid-injection syringe assembly according to claim 1, in which the syringe body is designed to be mounted so as to be axially movable inside the sheath between an active position in which the needle projects from a distal end of the sheath, and a protecting position in which the needle is retracted inside the sheath, the sheath including means designed to co-operate with complementary means of the plunger to secure the plunger and the sheath axially in a relative position of said plunger and said sheath serving firstly to position the body in its protecting position relative to the sheath, and secondly to position the plunger in its end-of-injection position relative to the body.

* * * * *